(12) United States Patent
Gronau et al.

(10) Patent No.: US 9,267,500 B2
(45) Date of Patent: Feb. 23, 2016

(54) METHOD AS WELL AS APPARATUSES FOR DETECTING A PERMEABILITY OR PATENCY IN A TUBE WHICH IS INSERTED IN A TUBE PUMP

(75) Inventors: Soeren Gronau, Nauheim (DE); Joachim Manke, Loehnberg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 248 days.

(21) Appl. No.: 13/559,734

(22) Filed: Jul. 27, 2012

(65) Prior Publication Data

US 2013/0030345 A1    Jan. 31, 2013

Related U.S. Application Data

(60) Provisional application No. 61/512,927, filed on Jul. 29, 2011.

(30) Foreign Application Priority Data

Jul. 29, 2011    (DE) .......................... 10 2011 108 778

(51) Int. Cl.
| | |
|---|---|
| *A61M 37/00* | (2006.01) |
| *F04B 51/00* | (2006.01) |
| *F04B 43/12* | (2006.01) |
| *A61M 1/10* | (2006.01) |
| *A61M 1/16* | (2006.01) |
| *A61M 1/36* | (2006.01) |

(52) U.S. Cl.
CPC .............. *F04B 51/00* (2013.01); *A61M 1/1039* (2014.02); *A61M 1/16* (2013.01); *F04B 43/1253* (2013.01); *A61M 1/3639* (2013.01); *A61M 2205/15* (2013.01); *A61M 2205/18* (2013.01); *A61M 2205/3331* (2013.01); *A61M 2205/3351* (2013.01); *A61M 2205/3355* (2013.01); *A61M 2205/70* (2013.01)

(58) Field of Classification Search
CPC .......... A61M 1/3639; A61M 2205/15; A61M 2205/18; A61M 2205/3331; A61M 2205/3351; A61M 2205/3355; F04B 43/082
USPC ...................................... 604/4.01, 5.01, 6.01
See application file for complete search history.

(56) References Cited

U.S. PATENT DOCUMENTS

| | | | | |
|---|---|---|---|---|
| 5,690,831 | A * | 11/1997 | Kenley et al. | ............... 210/646 |
| 5,695,473 | A | 12/1997 | Olsen | |
| 6,200,485 | B1 * | 3/2001 | Kitaevich et al. | ............ 210/739 |
| 7,004,924 | B1 * | 2/2006 | Brugger et al. | ............. 604/6.13 |

(Continued)

FOREIGN PATENT DOCUMENTS

| | | |
|---|---|---|
| DE | 102006011346 A1 | 9/2007 |
| DE | 102008029022 A1 | 4/2010 |

(Continued)

*Primary Examiner* — Tatyana Zalukaeva
*Assistant Examiner* — Andrew J Mensh
(74) *Attorney, Agent, or Firm* — Kenyon & Kenyon LLP

(57) ABSTRACT

The present invention relates to a method for detecting a permeability or patency of a section of an extracorporeal tube which is inserted in a tube pump, a detection device for executing a method according to the present invention, a medical treatment apparatus which comprises at least one detection device and/or is in signal transmission with it or is connected for signal transmission with it, a digital storage medium, a computer program product as well as a computer program.

15 Claims, 4 Drawing Sheets

(56) References Cited

U.S. PATENT DOCUMENTS

2001/0021817 A1* 9/2001 Brugger et al. .............. 604/6.11
2011/0230814 A1* 9/2011 Kopperschmidt et al. ... 604/6.11

FOREIGN PATENT DOCUMENTS

WO          2010020380 A1    2/2010
WO    WO 2010020380 A1 *   2/2010

* cited by examiner

METHOD AS WELL AS APPARATUSES FOR DETECTING A PERMEABILITY OR PATENCY IN A TUBE WHICH IS INSERTED IN A TUBE PUMP

CROSS-REFERENCE TO RELATED APPLICATIONS

The present application claims priority to, and the benefit of, U.S. Provisional Application 61/512,927 filed on Jul. 29, 2011. The contents of this provisional application is incorporated herein by reference in its entirety. The present application also claims priority to, and the benefit of, German Patent Application DE 10 2011 108 778.1 filed on Jul. 29, 2011. The contents of this foreign application is incorporated herein by reference in its entirety.

FIELD OF THE INVENTION

The present invention relates to methods and devices for detecting a permeability or patency of a section of an extracorporeal tube which is inserted in a tube pump.

BACKGROUND OF THE INVENTION

In addition to other fields of application, tube pumps are i.a. used in extracorporeal blood treatment such as dialysis to convey a fluid, in this case blood. Spring-loaded rollers which are to limit the maximum pressure of the pump—which additionally depends on the pump tube diameter—are state of the art. With increasing mechanical complexity of the pump rotor, the number of possible sources of failure usually increases, this is also true for tube pumps. Therefore, it is useful to check the proper functioning of the rotor. In WO 2010/020380 A1, a method is disclosed for monitoring the pump rotor during pump operation. Thereby, pressure gradients which are caused by the roller which is in mesh in the moment of observation are raised and compared with pressure gradients of other rollers. If deviations occur, a defect of the pump motor is concluded. A defect similarly affecting both (in the sense of all) rollers cannot, inherent to the functional principle, be detected. This is not the case using certain embodiments of the method according to the present invention. In such embodiments, defects and failures which lead to the improper performance of all involved displacers or the displacers which are checked for their functioning can advantageously also be detected. Such a failure can be—for example because of its tube diameter or material—the use of a tube which is not suitable for the concrete application. Further, such a failure can exist for example because of striations in the inner layer of the pump tube which can be caused through production faults. Because of the absolute measurements which are possible according to the present invention, which can be performed for each displacer independently from one another, a damage which can affect all displacers in the same way can be advantageously recognized.

As such one object of the present invention is to propose a further method for verification of the function of the displacers of a tube pump. In addition, suitable apparatuses, a suitable digital storage medium, a suitable computer program product and a suitable computer program are to be specified.

Thus, according to the present invention a method for detecting a permeability or patency of a section of an extracorporeal tube which is inserted in a tube pump and/or for verifying an occlusion effect of displacers of the tube pump on the tube, i.e. the flow rate in the longitudinal direction of the tube is proposed. The method according to the present invention encompasses the meshing of a displacer of the tube pump with the section of the tube in such a manner that the displacer reduces the permeability or patency of the lumen of the section for a fluid and/or the cross-sectional area of the section of the lumen. The method further encompasses building up, setting or effecting a first pressure or the effecting a first pressure change inside the tube on a first side of the section and/or the meshed displacer. Furthermore, the method according to the present invention encompasses measuring a second pressure or a second pressure change and/or evaluating a second pressure already measured or a second pressure change already measured respectively on a second side of the section and/or of the meshed displacer.

SUMMARY OF THE INVENTION

In one embodiment there is provided a method for detecting a permeability or patency of a section of an extracorporeal tube which is inserted in a tube pump, comprising the steps:
  meshing or engaging a displacer of the tube pump with a section of the tube such that the displacer reduces the permeability or patency of the section;
  effecting or changing a first pressure or a first pressure change inside the tube on a first side of the section and/or on a first side of the meshed displacer;
  evaluating a second pressure or a second pressure change which prevails or is measurable on a second side of the section and/or on a second side of the meshed displacer.

In an alternative embodiment the method further comprises stopping the tube pump in the position of the displacer in which it is meshed with the tube, for measuring a second pressure or a second pressure change.

In another embodiment the method further comprises the steps:
  determining the position of the meshed displacer by means of measurement signals and/or
  stopping the tube pump depending on the measurement signals with reference to the position of the displacer such that the displacer is meshed with the tube and/or stops in mesh.

In a further embodiment the method further comprises comparing the second pressure value or the second pressure change with previously stored values, threshold values, ranges or gradients.

In another embodiment there is provided a detection device for executing the method for detecting a permeability or patency of a section of an extracorporeal tube which is inserted in a tube pump.

In yet another embodiment there is provided a medical treatment apparatus which comprises at least one detection device and/or is in signal transmission with it or is connected for signal transmission, and which is embodied as a blood treatment apparatus, in particular as an apparatus for apheresis or dialysis, again in particular for hemodialysis, hemofiltration, hemodiafiltration.

In another embodiment there is provided a digital storage medium, in particular in the form of a disk, CD or DVD or EPROM, with electronically readable control signals, configured to interact with a programmable computer system such that the mechanical steps of the method for detecting a permeability or patency of a section of an extracorporeal tube which is inserted in a tube pump are prompted.

In yet another embodiment there is provided a computer program product with a program code stored on a machine-readable medium for prompting the mechanical steps of the method for detecting a permeability or patency of a section of an extracorporeal tube which is inserted in a tube pump, when the computer program product runs on a computer.

In another embodiment there is provided a computer program product with a program code for prompting the mechanical steps of the method for detecting a permeability or patency of a section of an extracorporeal tube which is inserted in a tube pump, when the computer program runs on a computer.

DETAILED DESCRIPTION

Figure 1:
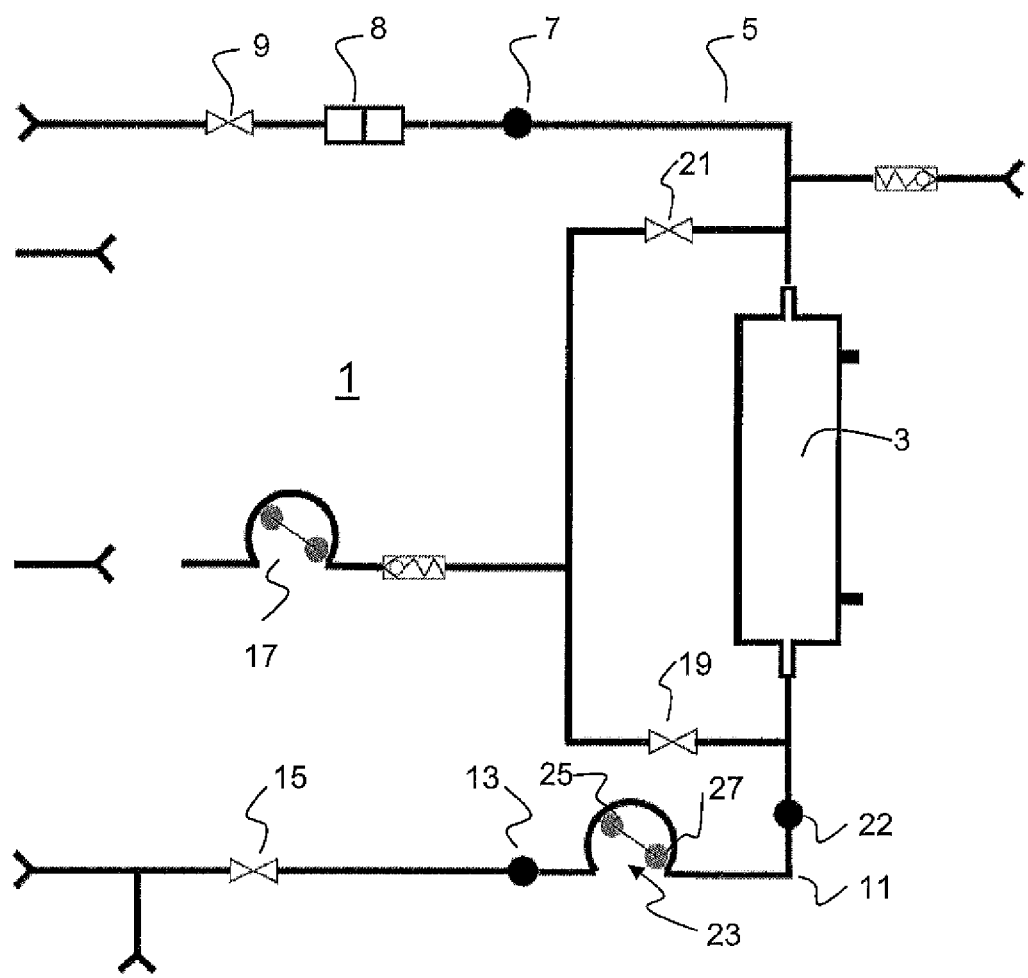
FIG. 1 shows a schematically simplified extracorporeal blood circuit with a tube pump, the occlusion effect of which can be checked by means of the method according to the present invention.

The detection device according to the present invention is suitable and intended and/or designed and/or configured for executing the method according to the present invention.

The medical or medical-technical treatment apparatus according to the present invention (in the following also abbreviated: treatment apparatus) comprises at least one detection device and/or is herewith connected in signal transmission or is in a signal transmission relation with it.

A digital, particularly a non-volatile storage medium according to the present invention, particularly in the form of a machine-readable data storage device, particularly in the form of a disk, CD, EPROM or DVD with electronically or optically readable control signals may interact with a programmable computer system such that the mechanical steps of the method according to the present invention are prompted.

In doing so, all, a few or some of the mechanically executed steps of the method according to the present invention can be prompted.

A computer program product according to the present invention comprises a program code stored on an machine-readable medium for prompting the mechanical steps of the method according to the present invention when the computer program runs on a computer. According to the present invention a computer program product can be understood as, for example, a computer program which is stored on a storage device, an embedded system as a comprehensive system with a computer program (e.g. an electronic device with a computer program), a network of computer-implemented computer programs (e.g. a client-server system, a cloud computing system, etc.), or a computer on which a computer product is loaded, executed, saved or developed.

The term machine-readable medium as used herein denotes in certain embodiments of the present invention a medium that contains data which is interpretable by software and/or hardware. The medium can be a data medium such as a disk, a CD, DVD, a USB stick, a flashcard, an SD card or the like.

A computer program according to the present invention comprises a program code for prompting the mechanical steps of the method according to the present invention when the computer program runs on a computer. A computer program according to the present invention can be understood as, for example, a physical software product, which is ready for distribution and contains a computer program.

I also applies to the computer program product and the computer program according to the present invention that all, a few or some of the mechanically executed steps of the method according to the present invention can be prompted.

In all of the following embodiments, it is to be understood that the use of the terms can be and respectively can have etc. are synonymous with is preferably and respectively has preferably etc. and is intended to explain an embodiment according to the present invention.

Embodiments according to the present invention can comprise one or more of the features mentioned in the following.

In some embodiments according to the present invention, the method serves to monitor or verify the tube pump or the functioning of any, some or all of the displacers of the tube pump.

In some embodiments according to the present invention, the method serves to detect or monitor a permeability or patency of the lumen of a section of an extracorporeal blood tube which is inserted in the tube pump.

In certain embodiments according to the present invention, the method serves to detect or monitor a permeability or patency of the lumen of the section which is inserted into the tube pump, of an extracorporeal blood tube.

In some embodiments according to the present invention, the method serves to detect or monitor a permeability or patency of the lumen of that section of a extracorporeal blood tube with which the displacer or the displacers is or are meshed or engaged for executing the method according to the present invention.

In certain embodiments according to the present invention, the tube pump is a peristaltic pump, e.g. a roller pump. The tube pump is in certain embodiments according to the present invention a blood pump.

In some embodiments according to the present invention the method according to the present invention is being conclusively executed with regard to one specific displacer while only this displacer (but not any other displacers of the tube pump) is compressing or reducing the lumen of the tube.

In certain embodiments according to the present invention the steps of the method according to the present invention are executed in the order described herein.

In some embodiments according to the present invention the at least one displacer is located on a rotor and/or is moveable or slidable during use relatively to the tube (in a longitudinal direction of or tangentially to the tube).

In certain embodiments according to the present invention, the method encompasses meshing exactly one or only one of the displacers of the tube pump with the section of the tube, in other embodiments the simultaneous meshing of several displacers.

Meshing can mean in some embodiments according to the present invention a complete or partial prevention of the permeability or patency of the lumen of the section for a fluid in its longitudinal extension, in particular for a medical fluid which is to be treated, or for a measuring fluid such as air, dialysate or substitute.

In some embodiments according to the present invention a displacer is not a valve.

In certain embodiments according to the present invention, the first pressure is a defined, known or predetermined pressure.

In some embodiments according to the present invention, the first pressure is an overpressure, in other embodiments according to the present invention it is a negative pressure.

In some embodiments according to the present invention, a first pressure change is a pressure rise, in other embodiments according to the present invention a pressure drop.

In some embodiments according to the present invention, the pressure rise or pressure drop is effected by means of a substitute pump and if necessary the interruption of fluid connections, for example by means of closing off or actuating valves or throttles, in particular to produce two closed tube segments which are sealed against further tube sections.

In certain embodiments according to the present invention evaluating the pressure, e.g. by a pressure sensor, may take place between the source of the pressure by which the first pressure or pressure change is being effected or changed, and the displacer.

In some embodiments according to the present invention the pressure is or was measured between the displacer and a tube clamp, which blocks the tube (or reduces its lumen), e.g. the arterial or venous tube clamp.

In certain embodiments according to the present invention, the first side lies—relative to the conveying direction during normal operation of the tube pump—downstream of the section which is meshed with the displacer. In these embodiments, the second side lies upstream of the section. In other embodiments according to the present invention, the first side lies upstream. The second side in these embodiments lies downstream of this section.

In some embodiments according to the present invention, evaluating a second pressure or a second pressure change over the time encompasses a corresponding measurement, in others no measurement is performed, but it is reverted to already measured values or values which are otherwise known. In doing so, a pressure value can be a direct specification for a pressure, for example in the form of a measured result. According to the present invention, however, under a pressure value also a different value than a pressure can be understood, from which the pressure is concluded or a pressure can be calculated.

In certain embodiments according to the present invention the second pressure or the second pressure change is measured for example by means of silicon piezoresistive sensors, piezoelectric sensors, diaphragm gauges, bending beam sensors or force sensing resistors.

In some embodiments according to the present invention, the second pressure change can be, as the first pressure change, a pressure drop, in others a pressure rise.

In some embodiments according to the present invention, the method encompasses stopping the tube pump in the position in which the displacer is meshed with the tube. In this condition, that is at standstill, thus a not conveying or rotating tube pump, the second pressure or the second pressure change can be measured in these embodiments.

In certain embodiments according to the present invention, the method encompasses determining the position of the meshed displacer with reference to a section of the tube or a section of the pump rotor bed or the stator of the tube pump. Additionally or alternatively, it encompasses stopping the tube pump such that the displacer is in the desired position, for example partly, fully or at maximum meshed with the tube.

In certain embodiments according to the present invention, the positioning is performed by means of one or more magnets and/or one or more Hall sensors in a known way or in a way which is described hereafter.

In some embodiments according to the present invention, the method encompasses comparing the second pressure value, the second pressure change or the second pressure gradient with corresponding values or gradients previously stored.

In certain embodiments according to the present invention, the method comprises providing a statement whether a pressure holding test has been passed or not. The statement may be provided based on the result of the comparison with corresponding values or gradients previously stored.

In some embodiments according to the present invention, the method is executed with each of the displacers which are meshed with the tube during the operation of the tube pump. In some embodiments according to the present invention, this takes place separately and independently for the respective displacers.

In certain embodiments according to the present invention, the method is executed and where required completed before the commencement of a treatment of a patient in which the tube pump is used.

In some embodiments according to the present invention, the method is not performed during the treatment of the patient.

The detection device according to the present invention is in some embodiments configured, provided and/or programmed for detecting an occlusion effect of a displacer of a tube pump on a section of a tube which is inserted in the tube pump.

In certain embodiments according to the present invention, the detection device is a monitoring device, a regulating or control device, a monitor or computing device.

In certain embodiments according to the present invention, the detection device comprises actuating devices, measuring devices, control devices or regulating devices, evaluating devices, comparison devices and/or storage devices for comparative data.

In some embodiments according to the present invention, the detection device comprises at least one display device for displaying a result of the execution of the method according to the present invention.

In certain embodiments according to the present invention, the detection device comprises at least one alarm device for outputting an alarm which is intended and/or configured for outputting an alarm in the event that the second pressure or the second pressure gradient does not lie in a predetermined range, gradient or value range, or beyond upper and/or lower limit values, or does not satisfy predetermined otherwise conditions.

In some embodiments according to the present invention a pressure gradient is the gradient of the pressure over lapse of time.

The treatment apparatus according to the present invention is in some embodiments designed as a blood treatment apparatus, in particular as an apparatus for apheresis or dialysis, again in particular for hemodialysis, hemofiltration, hemodiafiltration or for acute dialysis.

In some embodiments according to the present invention of the treatment apparatus, at least one of the displacers is embodied as a roller and the peristaltic tube pump is embodied as a roller pump.

In some embodiments according to the present invention, the method is executed when the pump is not running.

Some or all embodiments according to the present invention can comprise one or more of the above or the following advantages.

For example, since the method according to the present invention can be performed while preparing or setting up the treatment apparatus, a technical error can already be recognized before the patient is connected and before blood has come into contact with the apparatus as well as the extracorporeal blood circuit. The latter avoids an unnecessary increased use of disposable articles. It further allows a simple, as it takes place at an early stage, exchange of defective components in the event of faults.

Due to the measuring arrangement, a small measuring volume or a short section of the tube which is occluded to the first side by means of the displacer to be tested can very accurately measure.

In addition to other fields of application, tube pumps are i.a. used in extracorporeal blood treatment such as dialysis to convey a fluid, in this case blood. Spring-loaded rollers which are to limit the maximum pressure of the pump—which additionally depends on the pump tube diameter—are state of the art. With increasing mechanical complexity of the pump rotor, the number of possible sources of failure usually increases, this is also true for tube pumps. Therefore, it is useful to check the proper functioning of the rotor. In WO 2010/020380 A1, a method is disclosed for monitoring the pump rotor during pump operation. Thereby, pressure gradients which are caused by the roller which is in mesh in the moment of observation are raised and compared with pressure gradients of other rollers. If deviations occur, a defect of the pump motor is concluded. A defect similarly affecting both (in the sense of all) rollers cannot, inherent to the functional principle, be detected. This is not the case using certain embodiments of the method according to the present invention. In such embodiments, defects and failures which lead to the improper performance of all involved displacers or the displacers which are checked for their functioning can advantageously also be detected. Such a failure can be—for example because of its tube diameter or material—the use of a tube which is not suitable for the concrete application. Further, such a failure can exist for example because of striations in the inner layer of the pump tube which can be caused through production faults. Because of the absolute measurements which are possible according to the present invention, which can be performed for each displacer independently from one another, a damage which can affect all displacers in the same way can be advantageously recognized.

In this way, besides monitoring the functioning of the displacers, also monitoring the function or a quality control of the pump tube can also be performed. Advantageously, for this no separate test and no separate method steps are to be performed.

Furthermore according to the present invention it is also possible to recognize a functional impairment of only one displacer. In addition to the previously described absolute measurement, a relative measurement is thus also possible. For example, by the use of extendable rollers using certain embodiments of the present invention it can be proven that all the checked rollers can be extended fully or according to the intended use. This can be proven by means of each the measured occlusion pressure—for example with the non-running pump—when this meets certain criteria before, e.g., lies above the allowable second pressure or the test pressure or its gradient. Mechanical defects at the pump rotor such as jammed links or a broken spring which only affect single rollers, fingers or pins can be detected in this manner. Furthermore, a production defect can be detected, consisting of for example the use of too soft or otherwise unsuitable springs at one or all the rollers.

A not or not completely occluding blood pump can possibly lead in addition to a deviation of the conveying rate and an also undesired reverse conveying from the section compressed by the displacer to a deterioration of the extracorporeally conveyed blood. Also such defects or risks can be detected at an early stage by means of the method according to the present invention.

The present invention is exemplarily described in the following with the help of the appended drawings, in which identical reference numerals indicate same or similar components.

FIG. 1 shows a schematically simplified extracorporeal blood circuit 1, which is part of a blood cassette. The blood circuit 1 is embodied or connected with at least one dialyzer 3, a venous pressure measurement device 7 arranged in a venous blood line 5, an optical detector or air bubble detector 8, a venous clamp 9, an arterial pressure measurement device 13 arranged in an arterial blood line 11, an arterial clamp 15, a substitute pump 17, a predilution valve 19, and a postdilution valve 21.

The arterial blood line 11 comprises a measuring point 22 which is suitable or intended for measuring a pre-filter pressure or a pressure which prevails in front of or upstream of the dialyzer 3. Further devices primarily such as ports and connectors—as well as their position which is caused by the form of the blood cassette—are to be seen in FIG. 1, however, they are not relevant to the present invention.

Relevant to the present invention is however the tube pump denoted with the reference numeral 23 for conveying blood, which as the substitute pump 17 is part of a treatment apparatus according to the present invention and can be checked by means of the method according to the present invention. The tube pump 23 is exemplarily designed as a roller pump. It recognizably comprises in the example of FIG. 1 as examples of displacers, two distinguishable rollers 25 and 27. For the person skilled in the art, it is already recognizable in FIG. 1 that the number of displacers or rollers 25, 27 is not limited to two according to the present invention. Also three or more displacers or rollers can be provided and checked according to the present invention. Further, it is recognizable for the person skilled in the art that the present invention is not limited to checking a tube pump which operates in a circular motion. Indeed the method according to the present invention is for example also provided for the use at a tube pump which conveys by means of finger, not by means of rollers. An example of such pumps is disclosed in U.S. Pat. No. 6,558,347 B1.

Figure 2:
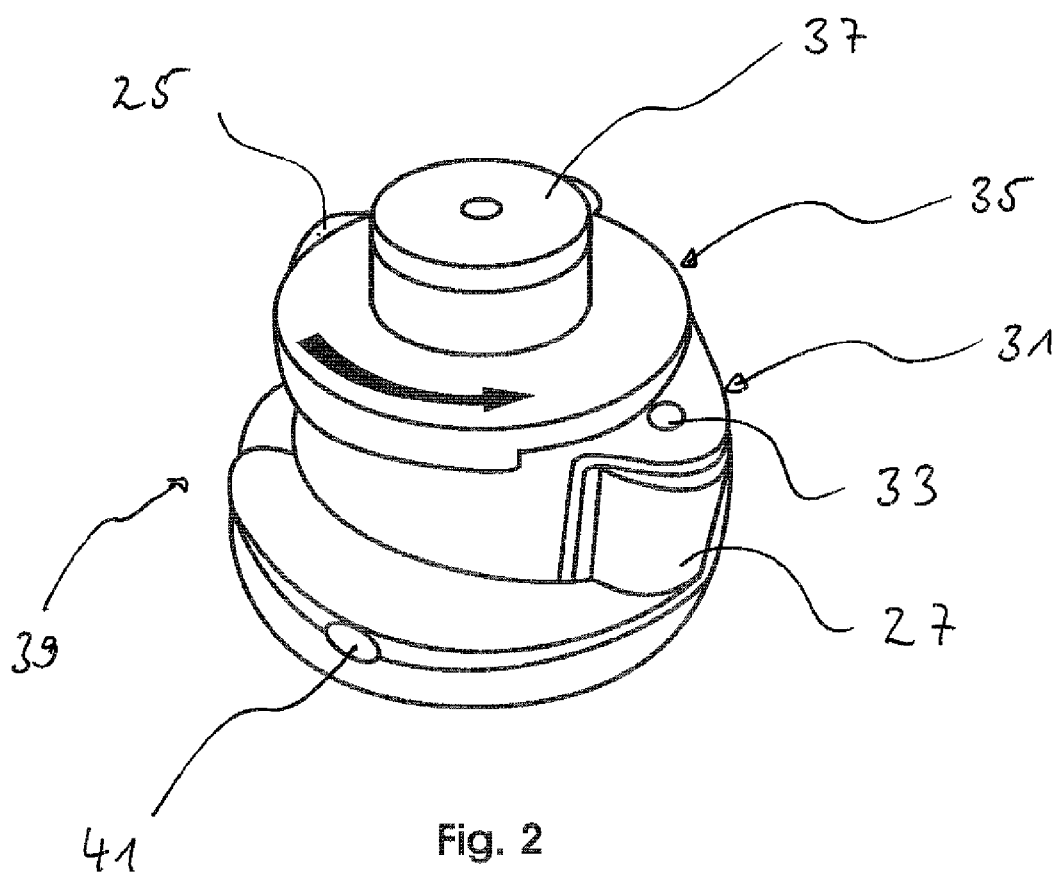
FIG. 2 shows a pump rotor, which can be a part of a tube pump of a treatment apparatus according to the present invention, in perspective view lying on the rear, the connecting face.

FIG. 2 shows in a front perspective view from above a pump rotor 31 which can be part of a tube pump of a blood treatment apparatus according to the present invention. The pump rotor 31 exemplarily comprises two rollers 25 and 27 which are each mounted by means of an axis 33. It could, however, also be provided with more than two rollers. The rollers could have a different form. They would not have to be mounted by means of axes.

The upper part 35 which is during use of the pump rotor 31 facing away from the treatment apparatus is furnished with a turning knob 37 for manual rotatability of the pump rotor 31. For example during the insertion of the blood tube, not shown in FIG. 2, into the tube pump, the pump rotor 31 can be turned by hand by means of the turning knob 37.

Figure 3:
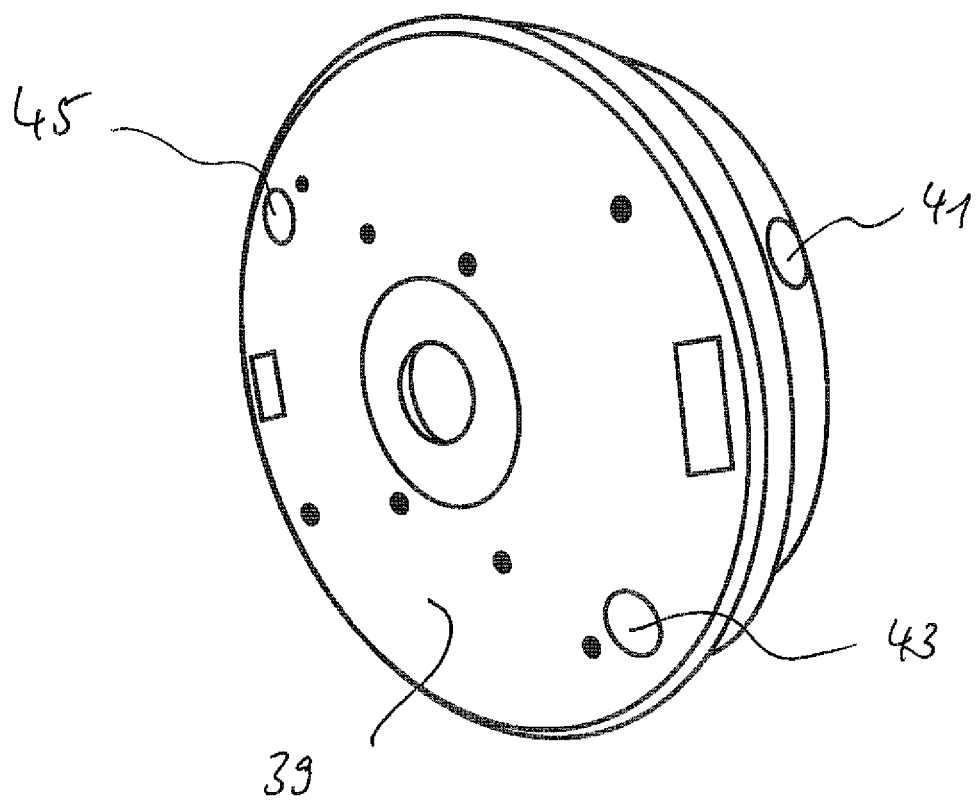
FIG. 3 shows the pump rotor of FIG. 2 in a side view on its connecting face.

On its lower part 39, the part of the pump rotor 31 which faces the treatment apparatus on the part facing the pump rotor 31 during operation of the pump rotor 31, the pump rotor 31 comprises three magnets in different magnet positions. However, also more than three magnet positions could be provided, in particular the number of magnet positions can correlate with the number of rollers provided. One of the magnet positions exemplarily provided here, the magnet position 41, is to be seen in FIG. 2. It is incorporated in a front of the lower part 39. The remaining two magnet positions 43 and 45 lie on or in the lower front face of the pump rotor and thus on or in a coupling face, by means of which the pump rotor 31 is functionally connected (coupled) to the treatment apparatus. The remaining two magnet positions 43 and 45 are therefore not visible in FIG. 2. They are however visible in FIG. 3, which shows the pump rotor 31 of FIG. 2 in a side view from behind and hence on the coupling face.

The pump rotor bed not shown in the figures comprises in total two Hall sensors at appropriate locations. A first Hall sensor is located on a front of the pump rotor bed, a second Hall sensor is located on the coupling face of the lower part 39 of the pump rotor 31, the rotor base.

If the single magnet position 41 provided on the side of the pump rotor 31 is moved past the first Hall sensor, the absolute position and thus the roller in mesh with the tube at this point in time can be determined.

For a fine resolution of the rotor position, in certain embodiments according to the present invention the pump motor generates a tacho signal. With the help of this, the angle passed since the last Hall sensor pass can be determined provided that the number of tacho pulses per angular degree is known.

With these sensors, the position of the pump rotor 31 can be determined with sufficient accuracy. Also, on this basis the pump rotor 31 can hereupon be positioned as desired.

Alternatively, for positioning the first roller 25, one of the magnets of the magnet positions 43 and 45 located on the coupling face of the lower part 39 of the pump rotor 31, the rotor base, can be moved past the second Hall sensor. Subsequently, the pump rotor 31 can be turned a further 180° around its rotational axis by means of the tacho signal to check the second roller 27.

Figure 4:
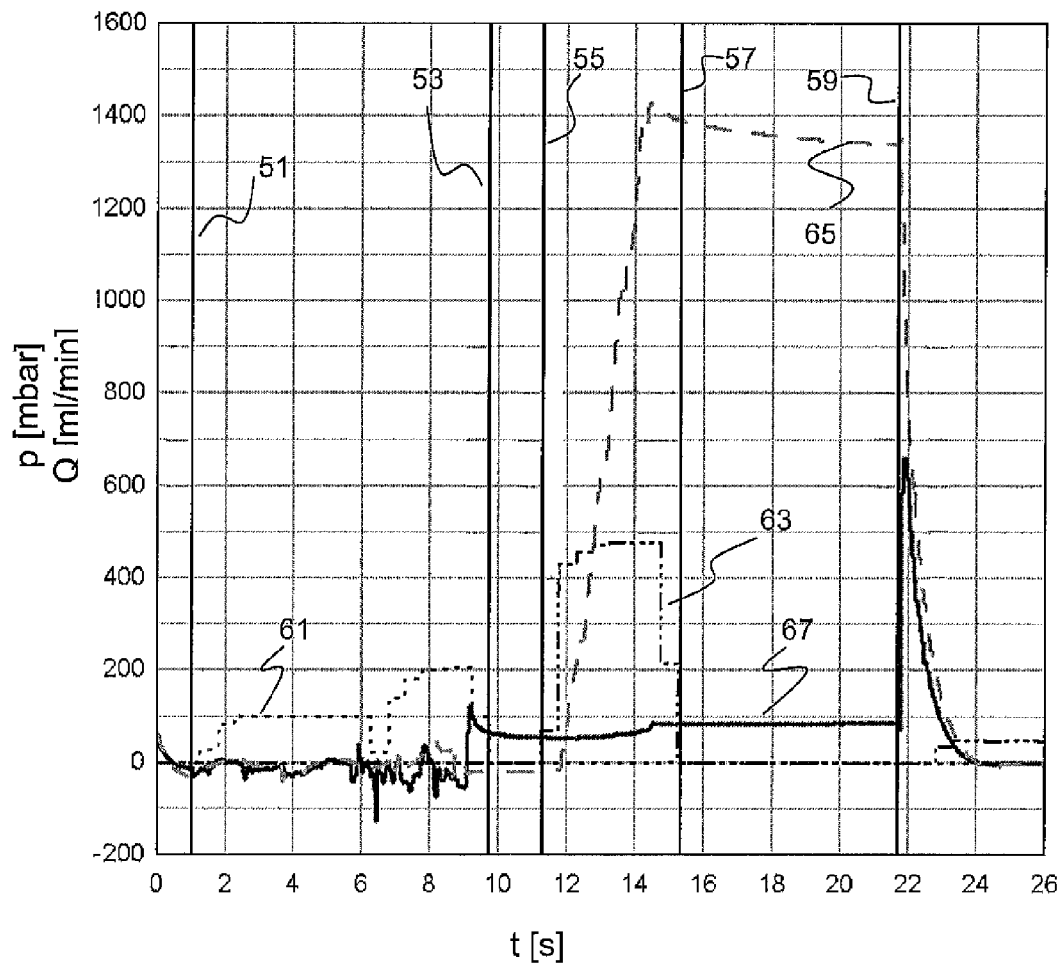
FIG. 4 shows pressure- and volume flow relationships or pressure and volume flow changes when executing the method according to the present invention.

FIG. 4 shows pressure and volume flow relationships or pressure and volume flow changes as well as their gradients during a roller measurement or roller check by means of the method according to the present invention. Hereby, respectively a blood pump flow 61 and a substitute pump flow 63 are specified in ml/min. A pressure 65 before the pump and a pressure 67 after the pump respectively are given in mbar.

After the extracorporeal blood circuit 1 of FIG. 1 was filled and bled of air, its tightness is tested—even before the patient is connected. In parallel, the method according to the present invention which in the embodiment described here can also be designated as a rotor stillstand leak check as the checked tube pump is not running at that time, is executed.

To perform the occlusion check described here, initially one of the two rollers, e.g., the first roller 25 is brought into mesh with the tube. This can be carried out, after the positioning, with the help of one or both of the above described Hall sensors to detect the angular position of the pump rotor 31, as described above.

In the illustration of FIG. 4, the positioning of the first roller 25 during which time this is brought into mesh with the tube, starts with the point in time marked with reference numeral 51 and finishes at the point in time marked with the reference numeral 53. After the positioning, only one roller, here roller 25, is meshed with the tube not shown on the figures.

In this condition, the arterial clamp 15 and the venous clamp 9 are closed. Dialysate supply valves and dialysate outlet valves from and to the dialyzer are also closed. Hence, a first and a second tube segment neither of which is in fluid communication with other tube sections or are closed off from these, are created.

Using the substitute pump 17, which now conveys, a first pressure in the first tube segment of the extracorporeal blood circuit 1 between tube pump 23 and venous clamp 9 can now be built up. The volume compartment of the second tube segment which is enclosed between roller 25 of the pump and arterial clamp 15 is small and has a low compliance (high stiffness), whereby even small amounts of fluid transfer into the second tube segment cause high pressure changes there. In the second tube segment, a second pressure is measured.

The start of the pressure build up in the first tube segment, that is on the first side, begins at the point in time marked with the reference numeral 55. Simultaneously or shortly thereafter, the evaluation of the pressure rise in the second tube segment, that is on the second side, begins. At the point in time indicated by reference numeral 57 or shortly before, the pressure build-up finishes. At the point in time 59 the pressure relief begins, the pressure rise evaluation then finishes.

During the pressure build-up-and-holding time, the pressure between the arterial clamp 15 and roller 25, measured with the arterial pressure measuring device 13, is evaluated. If its change exceeds a defined limit value (e.g., 200 mmHg), the test fails. A corresponding display and/or warning or a corresponding alarm (optical, acoustic, partial shut-down of the system etc.) can take place. A defect in the pump rotor 31 or a problem with the tube cannot be excluded.

If the check is passed,—the pressure does not exceed the allowable value during the check period,—the check of the first roller 25 is completed. The pressure in the extracorporeal blood circuit 1 is relieved by opening the venous clamp 9 and checking of the second roller 27 is prepared.

To check the second roller 27, it is sufficient to turn the pump rotor by 180°, whereby due to the symmetry of the pump rotor 31 the second roller 27 is positioned exactly. There is of course also the possibility of using the Hall sensors to assist in performing an absolute positioning of the second roller 27.

After the positioning of the second roller 27, the outline procedure for checking the first roller 25 is run through again. If the test, and thus the method according to the present invention, was passed also for the second roller 27, further tests or the preparation of the apparatus for connection to a patient can be proceeded with.

The invention claimed is:

1. A method for detecting a permeability or patency of a section of an extracorporeal tube which is inserted in a tube pump, comprising the steps:
   meshing or engaging one displacer of a plurality of displacers of the tube pump with a section of the tube such that the one displacer reduces the permeability or patency of the section;
   effecting or changing a first pressure or a first pressure change inside the tube on at least one of a first side of the section or a first side of the meshed displacer;
   evaluating a second pressure or a second pressure change which prevails or is measureable on at least one of a second side of the section or a second side of the meshed displacer,
   comparing the second pressure or the second pressure change with previously stored values, threshold values, ranges or gradients of the meshed displacer; and
   executing the method while only the one displacer of the plurality of displacers comes into mesh or engagement with the section of the tube during the operation of the tube pump.

2. The method according to claim 1, further comprising the step:
   stopping the tube pump in the position of the displacer in which it is meshed with the tube, for measuring the second pressure or the second pressure change.

3. The method according to claim 1, further comprising at least one of the following steps:
  determining the position of the meshed displacer by means of measurement signals; or
  stopping the tube pump depending on the measurement signals with reference to the position of the displacer such that the displacer is at least one of meshed with the tube or stopped in mesh.

4. The method according to claim 1, further comprising the step:
  executing the method with each of the displacers which come into mesh with the tube during the operation of the tube pump.

5. The method according to claim 1, whereby the method is executed before commencement of a treatment of a patient in which the tube pump is used.

6. A detection device for executing the method according to claim 1.

7. The detection device according to claim 6, comprising at least one display device for displaying a result of the execution of the method according to claim 1.

8. The detection device according to claim 6, comprising at least one alarm device for outputting, wherein the alarm device is provided for outputting an alarm in the event that the result of the execution of the method according to claim 1 does not lie in a predetermined values range or range.

9. A medical treatment apparatus comprising at least one detection device according to claim 6 and/or is in signal transmission with it or is connected for signal transmission.

10. The medical treatment apparatus according to claim 9 which is embodied as a blood treatment apparatus for apheresis, dialysis, hemodialysis, hemofiltration, or hemodiafiltration.

11. The medical treatment device according to claim 9 wherein at least one of the displacers is designed as a roller and whereby the tube pump is designed as a roller pump.

12. A non-transitory digital storage medium with electronically readable control signals, configured to interact with a programmable computer system such that the mechanical steps of the method according to claim 1 are prompted.

13. The digital storage medium according to claim 12 in the form of a disk, CD or DVD or EPROM.

14. The method according to claim 3, further comprising the step:
  executing the method with each of the displacers which come into mesh with the tube during the operation of the tube pump.

15. A non-transitory computer-readable medium with an executable program stored thereon, wherein the program instructs a programmable computer system to execute the method according to claim 1.

* * * * *